(12) United States Patent
Voronkov et al.

(10) Patent No.: US 7,105,050 B2
(45) Date of Patent: Sep. 12, 2006

(54) METHOD FOR THE PRODUCTION OF LOW DEFECT DENSITY SILICON

(75) Inventors: Vladimir V. Voronkov, Merano (IT); Robert J. Falster, London (GB); Mohsen Banan, Grover, MO (US)

(73) Assignee: MEMC Electronic Materials, Inc., St. Peters, MO (US)

( * ) Notice: Subject to any disclaimer, the term of this patent is extended or adjusted under 35 U.S.C. 154(b) by 0 days.

(21) Appl. No.: 11/058,885

(22) Filed: Feb. 16, 2005

(65) Prior Publication Data

US 2005/0132948 A1    Jun. 23, 2005

Related U.S. Application Data

(62) Division of application No. 09/972,608, filed on Oct. 5, 2001, now Pat. No. 6,858,307.

(60) Provisional application No. 60/252,715, filed on Nov. 22, 2000, provisional application No. 60/245,610, filed on Nov. 3, 2000.

(51) Int. Cl.
    *C30B 15/20*    (2006.01)

(52) U.S. Cl. .............................. 117/20; 117/13; 117/15; 117/19

(58) Field of Classification Search .................. 117/13, 117/15, 19, 20
    See application file for complete search history.

(56) References Cited

U.S. PATENT DOCUMENTS

| | | |
|---|---|---|
| 3,997,368 A | 12/1976 | Petroff et al. |
| 4,314,595 A | 2/1982 | Yamamoto et al. |
| 4,981,549 A | 1/1991 | Yamashita et al. |
| 5,264,189 A | 11/1993 | Yamashita et al. |
| 5,474,020 A | 12/1995 | Bell et al. |
| 5,485,803 A | 1/1996 | Habu |
| 5,487,354 A | 1/1996 | von Ammon et al. |
| 5,502,010 A | 3/1996 | Nadahara et al. |
| 5,667,584 A | 9/1997 | Takano et al. |
| 5,704,973 A | 1/1998 | Sakurada et al. |
| 5,728,211 A | 3/1998 | Takano et al. |
| 5,919,302 A | 7/1999 | Falster et al. |
| 5,935,320 A | 8/1999 | Graef et al. |
| 5,942,032 A | 8/1999 | Kim et al. |

(Continued)

FOREIGN PATENT DOCUMENTS

DE     43 23 964 A1     1/1994

(Continued)

OTHER PUBLICATIONS

Abe, T., et al., "Swirl Defects in Float-Zoned Silicon Crystals," Physics., vol. 116B, (1983), pp. 139-147.

(Continued)

*Primary Examiner*—Felisa Hiteshew
(74) *Attorney, Agent, or Firm*—Senniger Powers (57) ABSTRACT

A process for the preparation of a silicon single ingot in accordance with the Czochralski method. The process for growing the single crystal silicon ingot comprises controlling (i) a growth velocity, v, (ii) an average axial temperature gradient, $G_O$, during the growth of a constant diameter portion of the crystal over a temperature range from solidification to a temperature of no less than about 1325° C. to initially produce in the constant diameter portion of the ingot a series of predominant intrinsic point defects including vacancy dominated regions and silicon self interstitial dominated regions, alternating along the axis, and cooling the regions from the temperature of solidification at a rate which allows silicon self-interstitial atoms to diffuse radially to the lateral surface and to diffuse axially to vacancy dominated regions to reduce the concentration intrinsic point defects in each region.

36 Claims, 3 Drawing Sheets

U.S. PATENT DOCUMENTS

| | | | |
|---|---|---|---|
| 5,954,873 | A | 9/1999 | Hourai et al. |
| 5,968,262 | A | 10/1999 | Saishouji et al. |
| 5,968,264 | A | 10/1999 | Iida et al. |
| 6,045,610 | A | 4/2000 | Park et al. |
| 6,053,974 | A | 4/2000 | Luter et al. |
| 6,093,913 | A | 7/2000 | Schrenker et al. |
| 6,153,008 | A | 11/2000 | von Ammon et al. |
| 6,228,164 | B1 | 5/2001 | von Ammon et al. |
| 6,236,104 | B1 | 5/2001 | Falster et al. |
| 6,379,642 | B1 | 4/2002 | Falster et al. |
| 6,500,255 | B1 | 12/2002 | Falster et al. |
| 6,565,649 | B1 | 5/2003 | Mule'Stagno et al. |

FOREIGN PATENT DOCUMENTS

| | | |
|---|---|---|
| DE | 44 14 947 A1 | 8/1995 |
| DE | 198 06 045 A1 | 8/1998 |
| EP | 0 504 837 A2 | 9/1992 |
| EP | 0 536 958 A1 | 4/1993 |
| EP | 0 716 168 A1 | 6/1996 |
| EP | 0 503 816 B1 | 9/1996 |
| EP | 0 747 513 A2 | 12/1996 |
| EP | 0 799 913 A1 | 10/1997 |
| EP | 0 890 662 A1 | 1/1999 |
| EP | 0 909 840 A1 | 4/1999 |
| EP | 0 962 556 A1 | 8/1999 |
| EP | 0 962 557 A1 | 12/1999 |
| EP | 0 990 718 A1 | 4/2000 |
| GB | 2 137 524 A | 10/1984 |
| GB | 2 182 262 A | 5/1987 |
| JP | HEI 2-180789 A | 7/1990 |
| JP | HEI 2-267195 A | 10/1990 |
| JP | HEI 3-93700 A | 4/1991 |
| JP | HEI 4-042893 | 2/1992 |
| JP | HEI 4-108682 A | 4/1992 |
| JP | HEI 7-041383 A | 2/1995 |
| JP | HEI 7-206591 A | 8/1995 |
| JP | HEI 8-012493 A | 1/1996 |
| JP | HEI 8-208374 A | 8/1996 |
| JP | HEI 8-268794 | 10/1996 |
| JP | HEI 8-330316 | 12/1996 |
| JP | HEI 9-202690 | 8/1997 |
| JP | HEI 11-157995 A | 6/1999 |
| JP | HEI 11-180800 A | 7/1999 |
| JP | HEI 11-189495 A | 7/1999 |
| JP | HEI 11-199386 A | 7/1999 |
| JP | HEI 11-199387 A | 7/1999 |
| WO | WO 97/26393 | 7/1997 |
| WO | WO 98/45507 | 10/1998 |
| WO | WO 98/45508 | 10/1998 |
| WO | WO 98/45509 | 10/1998 |
| WO | WO 98/45510 | 10/1998 |
| WO | WO 00/13211 | 3/2000 |
| WO | WO 01/21861 | 3/2001 |
| WO | WO 01/21864 | 3/2001 |
| WO | WO 01/21865 | 3/2001 |

OTHER PUBLICATIONS

Abe, T., et al., "The Characteristics of Nitrogen in Silicon Crystals," VLSI Science and Technology/1985, (Electrochem. Soc. Pennington, 1985), Proceedings vol. 85-5, (1985), pp. 543-551.

Abe, T., "The formation mechanism of grown-in defects in CZ silicon crystals based on thermal gradients measured by thermocouples near growth interfaces", Materials Science and Engineering, vol. B73 (2000), pp. 16-29.

Abe, T., et al., "Behavior of Point Defects in FZ Silicon Crystals," Semiconductor Silicon 1990, Proceedings of the Sixth International Symposium of Silicon Materials Science and Technology, vol. 90-7 (1990), pp. 105-116.

Abe, T., et al., "Dynamic Behavior of Intrinsic Point Defects in FZ and CZ Silicon Crystals," Mat. Res. Soc. Symp. Proc., vol. 262, (1992), pp. 3-13.

Borionetti, G., et al., "Investigation on Low Density Defects in Czochralski Silicon Crystals: Their Detectability, Formation Kinetics and Influence on Gate Oxide Integrity," Electrochemical Society Proceedings, vol. 96-13, pp. 160-169.

De Kock, A.J.R., "Microdefects in Swirl-Free Silicon Crystals," pp. 83-94 (source unknown) (date unknown).

De Kock, A.J.R., "The Elimination of Vacancy-Cluster Formation in Dislocation -Free Silicon Crystals," J. of the Electrochem. Soc.: Solid-State Science and Technology, vol. 118, No. 11, (Nov. 1971), pp. 1851-1856.

De Kock, A.J.R., et al., "Effect of Growth Parameters on Formation and Elimination of Vacancy Clusters in Dislocation-Free Silicon Crystals," Journal of Crystal Growth, vol. 22 (1974), pp. 311-320.

De Kock, A.J.R., "Point Defect Condensation in Dislocation-Free Silicon Crystals", Semiconductor Silicon, 1977, pp. 508-520.

De Kock, A.J.R., et al., "The Effect of Doping on the Formation of Swirl Defects in Dislocation-Free Czochralski-Grown Silicon Crystals," Journal of Crystal Growth, vol. 49 (1980) pp. 718-734.

Dornberger, E., et al., "The Dependence of Ring Like Distributed Stacking Faults on the Axial Temperature Gradient Czochralski Silicon Crystals," Electrochemical Society Proceedings, vol. 95-4 (1995) pp. 294-305.

Dornberger, E., et al., "Simulation of Grown-in Voids in Czochralski Silicon Crystals," Electrochemical Society Proceedings, vol. 97, No. 22 pp. 40-49.

Dornberger, E. et al., "Simulation of Non-Uniform Grown-in Void Distributions in Czochralski Silicon Crystals," Electrochemical Society Proceedings, vol 98-1 (1998) pp. 490-503.

Dornberger, E., et al., "The Impact of Dwell Time Above 900 ° C. During Crystal Growth on the Gate Oxide Integrity of Silicon Wafers," Electrochemical Society Proceedings, vol. 96-13, pp. 140-151.

Eidenzon, A.M. et al., "Microdefects in Dislocation-Free Silicon Monocrystals," TSVAM Met., No. 3 (1984) pp. 64-67.

Eidenzon, A.M., et al., "Influence of Growth Rate on Swirl Defects in Large Dislocation-Free Crystals of Silicon Grown by the Czochralski Method," Sov. Phys. Crystallogr., vol. 30, No. 5 (1985) pp. 576-580, American Institute of Physics.

Eidenzon, A.M., et al., "Influence of Growth Microdefects on Formation of Microdefects During High-Temperature Treatment of Silicon," Sov. Phys. Crystallogr., vol. 31, No. 2 (1985) pp. 199-203, American Institute of Physics.

Eidenzon, A.M., et al., "Specific Microdefects in Dislocation-Free Silicon Doped with Phosphorus," Sov. Phys. Crystallogr., vol. 33, No. 4 (1988) pp. 561-565, American Institute of Physics.

Eidenzon, A.M., et al., "Interrelation Between Distributions of Growth- and Thermally- Induced Microdefects and Impurity Distribution in Dislocation-Free Silicon Grown by the Czochralski Method with a Constant Magnetic Field Acting on the Melt," Sov. Phys. Crystallogr., vol. 35, No. 2 (1990) pp. 250-254, American Institute of Physics.

Eidenzon, A.M., et al., "Classification of Grown-In Microdefects in Czochralski-Grown Silicon Crystals," Inorganic Materials, vol. 31(4), 1994, pp. 401-409.

Eidenzon, A.M., et al., "Defect-Free Silicon Crystals Grown by the Czochralski Technique," Inorganic Materials, vol. 33, No. 3 (1997) pp. 219-225, Interperiodica Publishing.

Falster, R., et al., Intrinsic Point-Defects and Reactions in the Growth of Large Silicon Crystals, Electrochemical Society Proceedings, vol. 98-1, pp. 468-489.

Foll, H., et al., "The Formation of Swirl Defects in Silicon by Agglomeration of Self-Interstitials," Journal of Crystal Growth, 1977, pp. 90-1087, vol. 40, North-Holland Publishing Company.

Harada, H., et al., Oxygen Precipitation Enhanced with Vacancies in Silicon, pp. 76-85.

Hourai, M., et al., "Nature and Generation of Grown-In Defects in Czochralski Silicon Crystals," Electrochemical Society Proceedings, vol. 98-1, pp. 453-467.

Hourai, M., et al., "Improvement of Gate Oxide Integrity Characteristics of CZ-Grown Silicon Crystals," Progress in Semiconductor Fabrication presented by: Semiconductor Equipment and Materials International, Semicon/Europa 93, Mar. 30-Apr. 1, 1993, Geneva, Switzerland.

Hourai, M., et al., "Growth Parameters Determining the Type of Grown-In Defects in Czochralski Silicon Crystals," Materials Science Forum, vols. 196-201 (1995) pp. 1713-1718.

Hourai, M., et al., "Formation Behavior of Infrared Light Scattering Defects in Silicon During Czochralski Crystal Growth," J. Electrochem. Soc., vol. 142(9), (1995), 3193-3201.

Kissinger, G., et al., "A Method For studying the Grown-In Defect Density Spectra in Czochralski Silicon Wafers," Journal of Electrochemical Society, vol. 144, No. 4 (1997) pp. 1447-1456.

Kitano, et al., "Identification of Vacancy Clusters in FZ-Si Crystals," Phys. Stat. Sol, vol. 127(a), (1991), 341-347.

Lemke, H., et al., "Analytical Approximations for the Distributions of Intrinsic Point Defects in Grown Silicon Crystals", Phys. Stat. Sol. (a) vol. 176 (1999), pp. 843-865.

Majima, et al., "High-Sensitivity Defect Evaluation by a New Preferential Etching Technique for Highly As-Doped Si Crystals," Jpn. J. Appl. Phys., vol. 36, No. 10 (1997) pp. 6195-6199.

Nagasima, et al., "Observation of Grown-In Defects in CZ-Si Crystal," Meeting of the Japan Society of Applied Physics (1993).

Nakamura, K., et al., "Formation Process of Grown-In Defects in Czochralski Grown Silicon Crystals," Journal of Crystal Growth, vol. 180 (1997) pp. 61-72.

Park, J.G., et al., "Effect of Crystal Defects on Device Characteristics," Electrochemical Society Proceedings, vol. 97-22 (Jul. 16, 1997), pp. 173-195.

Puzanov, N.I., et al., "Influence of Transitional Crystallization Regimes on Microdefects in Silicon," USSR Academy of Sciences Newsletter, vol. 22, No. 8 (1986), pp. 1237-1242.

Puzanov, N.I. et al. "The Effect Of Thermal History During Crystal Growth On Oxygen Precipitation In Czochralski-grown Silicon," Semicond. Sci. Technol., vol. 7 (1992) pp. 406-413.

Puzanov, N.I., et al., "Relaxation in a System of Point Defects in a Growing Dislocation-Free Crystal of Silicon," Sov. Phys. Crystallogr., vol. 31, No. 2 (1986) pp. 219-222, American Institute of Physics.

Puzanov, N.I., et al., "Role of Vacancies in the Nucleation of Ringlike-patterned Oxidation-induced Stacking Faults in Melt-grown Silicon Crystals" Inorganic Materials, vol. 34-4, (1998) pp. 307-314.

Puzanov, N.I., et al., "Influence of Growth Conditions on the Formation of Microdefects in Dislocation-Free Silicon," Sov. Phsys. Crystallogr., vol. 34(2), (1989) pp. 273-278.

Puzanov, N.I., et al., "Microdefects in Silicon Grown by the Czochralski Method with a Vertical Magnetic Field Acting on the Melt," Sov. Phys. Crystallogr. 35(1), (1990), pp. 102-105.

Puzanov, N.I. et al., "Effects of Silicon Monocrystal Growth Conditions on Oxygen Precipitation During High-Temperature Processing," vol. 37, No. 5 (1992) pp. 1-10.

Puzanov, N.I. et al. "Formation Of The Bands Of Anomalous Oxygen Precipitation In Czochralski-grown Si Crystals," Journal of Crystal Growth 137 (1994) pp. 642-652.

Puzanov, N.I. et al. "The Role Of Intrinsic Point Defects In The Formation Of Oxygen Precipitation Centers In Dislocation-Free Silicon," Crystallography Reports; vol. 41; No. 1(1996) pp. 134-141.

Puzanov, N.I., et al., "Cultivation, Morphology and Structural Integrity of Dislocation-Free Silicon Tetracrystals," Inorganic Materials, vol. 32, No. 8 (1996), pp. 903-912.

Puzanov, N.I., et al., "Modeling Point-Defect Distribution in Dislocation-Free Si Crystals Grown from the Melt," Inorganic Materials, Vo. 32(1), (1996), pp. 1-9.

Puzanov, N.I. et al. "Harmful Microdefects In The Seed-End Portion Of Large-Diameter Silicon Ingots," Inorganic Materials, vol. 33, No. 8 (1997) pp. 765-769.

Puzanov, N.I. et al. "Modeling Microdefect Distribution In Dislocation-Free Si Crystals Grown From The Melt," Journal of Crystal Growth 178 (1997) pp. 468-478.

Roksnoer, P.J., "Effect of Low Cooling Rates on Swirls and Striations in Dislocation-Free Silicon Crystals," vol. 35, (1976), pp. 245-248.

Roksnoer, P.J., "Microdefects in a Non-Striated Distribution in Floating-Zone Silicon Crystals," Journal of Crystal Growth, vol. 53 (1981), pp. 563-573.

Roksnoer, P.J., "The Mechanism of Formation of Microdefects in Silicon," Journal of Crystal Growth, vol. 68 (1984), pp. 596-612.

Ryuta, J, et al., "Crystal-Originated Singularities on Si Wafer Surface after SC1 Cleaning," Japanese Journal of Applied Physics, vol. 29(11) (1990), pp. L1947-L1949.

Seidel, T.E., "Silicon Wafers for the 1990's," Journal of Crystal Growth, vol. 85, (1987), pp. 97-105.

Shimanuki, Y., et al., "Effects of Thermal History on Microdefect Formation in Czochralski Silicon Crystals," Japanese Journal of Applied Physics, vol. 24, No. 12, (1985), pp. 1594-1599.

Sinno, T., et al., "On the Dynamics of the Oxidation-Induced Stacking-Fault Ring in As-Grown Czochralski Silicon Crystals," Applied Physics Letters, vol. 70, No. 17 (1997) pp. 2250-2252.

Sinno, T., et al., "Point Defect Dynamics and the Oxidation-Induced Stacking-Fault Ring in Czochralski-Grown Silicon Crystals," Journal of Electrochemical Society, vol. 145, No. 1 (1998) pp. 302-318.

Stutius, et al., "Growth and Doping of ZnSe and $ZnS_xSe_{1-x}$ by Organometallic Chemical Vapor Deposition," Journal of Crystal Growth, vol. 59 (1982) pp. 1-9.

Tan, T.Y., "Point Defects, Diffusion Processes, and Swirl Defect Formation in Silicon," Appl. Phys. A., vol. 37 (1985) pp. 1-17.

Vanhellemont, J., et al., "Defects in As-Grown Silicon and Their Evolution During Heat Treatments," Materials Science Forum, vols. 258-263 (1997) pp. 341-346.

Von Ammon, et al., "The Dependence of Bulk Defects on the Axial Temperature Gradient of Silicon Crystals During Czochralski Growth," Journal of Crystal Growth, vol. 151 (1995) pp. 273-277.

Von Ammon, et al., "Bulk properties of very large diameter silicon single crystals" Journal of Crystal Growth, vol. 198/199, (1999), pp. 390-398.

Voronkov, V., et al., "Behavior and Effects of Intrinsic Point Defects in the Growth of Large Silicon Crystals," Electrochemical Society Proceedings, vol. 97-22 (1997), pp. 3-17.

Voronkov, V., "The Mechanism of Swirl Defects Formation in Silicon," Journal of Crystal Growth, 59 (1982), pp. 625-643.

Wijaranakula, W., "Numerical Modeling of the Point Defect Aggregation during the Czochralski Silicon Crystal Growth," Journal of Electrochemical Society, vol. 139, No. 2 (Feb. 1992), pp. 604-616.

Wijaranakula, W., "Effect of High-Temperature Annealing on the Dissolution of the D-Defects in N-Type Czochralski Silicon, " Appl. Phys. Lett., vol. 64(8), (1994), 1030-1032.

Wijaranakula, W., "Fundamentals of Point Defect Aggregation and Dissolution Phenomena of Crystal Originated Defects in Czochralski Silicon," Materials Science Forum, vols. 196-201 (1995) pp. 1691-1696.

Winkler, R., et al., "Improvement of the Gate Oxide Integrity by Modifying Crystal Pulling and Its Impact on Device Failures," Journal of Electrochemical Society, vol. 141, No. 5 (1994) pp. 1398-1401.

Yamagishi, et al., "Recognition of D Defects in Silicon Single Crystals by Preferential Etching and Effect on Gate Oxide Integrity", Semicond. Sci Technol. 7, 1992, A135-A140.

Yamauchi, T., et al., "Application of Copper-Decoration Method to Characterize As-Grown Czochralski-Silicon," Jpn. J. Appl. Phys., vol. 31, (1992), pp. L439-L442.

Zimmerman, H., et al. "Gold and Platinum Diffusion: the Key to the Understanding of Intrinsic Point Defect Behavior in Silicon," Applied Physics A Solids and Surfaces, vol. A55, No. 1 (1992) pp. 121-134.

Zimmerman, H., et al., "Vacancy Concentration Wafer Mapping in Silicon," Journal of Crystal Growth 129 (1993) pp. 582-592.

PCT International Search Report for PCT/US01/44081 dated Aug. 28, 2002.

No Heat Treat
+ B-defect test

FIG. 4B 1250C, 10s
+ B-defect test

METHOD FOR THE PRODUCTION OF LOW DEFECT DENSITY SILICON

CROSS-REFERENCE TO RELATED APPLICATION

This is a divisional application of U.S. patent application Ser. No. 09/972,608, filed Oct. 5, 2001, now U.S. Pat. No. 6,858,307, which claims the benefit of U.S. Provisional Application No. 60/252,715, filed Nov. 22, 2000 and U.S. provisional application Ser. No. 60/245,610, filed Nov. 3, 2000, all of which are incorporated in their entirety herein by reference.

BACKGROUND OF THE INVENTION

The present invention generally relates to the preparation of semiconductor grade single crystal silicon which is used in the manufacture of electronic components. More particularly, the present invention relates to a process for producing a single crystal silicon ingot by the Czochralski method, a substantial portion of which is substantially free of agglomerated intrinsic point defects, wherein the crystal growth conditions are varied to initially create alternating regions of silicon self-interstitial dominated material and vacancy dominated material within the constant diameter portion of the ingot. The regions of vacancy dominated material act as sinks to which self-interstitials may diffuse and be annihilated.

Single crystal silicon, which is the starting material for most processes for the fabrication of semiconductor electronic components, is commonly prepared by the so-called Czochralski ("Cz") method. In this method, polycrystalline silicon ("polysilicon") is charged to a crucible and melted, a seed crystal is brought into contact with the molten silicon and a single crystal is grown by slow extraction. After formation of a neck is complete, the diameter of the crystal is enlarged by decreasing the pulling rate and/or the melt temperature until the desired or target diameter is reached. The cylindrical main body of the crystal which has an approximately constant diameter is then grown by controlling the growth rate and the melt temperature while compensating for the decreasing melt level. Near the end of the growth process but before the crucible is emptied of molten silicon, the crystal diameter is reduced gradually to form an end-cone. Typically, the end-cone is formed by increasing the crystal growth rate and heat supplied to the crucible. When the diameter becomes small enough, the crystal is then separated from the melt.

In recent years, it has been recognized that a number of defects in single crystal silicon form in the crystal growth chamber as the crystal cools after solidification. Such defects arise, in part, due to the presence of an excess (i.e. a concentration above the solubility limit) of intrinsic point defects, which are known as vacancies and self-interstitials. Silicon crystals grown from a melt are typically grown with an excess of one or the other type of intrinsic point defect, either crystal lattice vacancies ("V") or silicon self-interstitials ("I"). It has been suggested that the type and initial concentration of these point defects in the silicon are determined at the time of solidification and, if these concentrations reach a level of critical supersaturation in the system and the mobility of the point defects is sufficiently high, a reaction, or an agglomeration event, will likely occur. Agglomerated intrinsic point defects in silicon can severely impact the yield potential of the material in the production of complex and highly integrated circuits.

Vacancy-type defects are recognized to be the origin of such observable crystal defects as D-defects, Flow Pattern Defects (FPDs), Gate Oxide Integrity (GOI) Defects, Crystal Originated Particle (COP) Defects, crystal originated Light Point Defects (LPDs), as well as certain classes of bulk defects observed by infrared light scattering techniques such as Scanning Infrared Microscopy and Laser Scanning Tomography. Also present in regions of excess vacancies are defects which act as the nuclei for ring oxidation induced stacking faults (OISF). It is speculated that this particular defect is a high temperature nucleated oxygen agglomerate catalyzed by the presence of excess vacancies.

Defects relating to self-interstitials are less well studied. They are generally regarded as being low densities of interstitial-type dislocation loops or networks. Such defects are not responsible for gate oxide integrity failures, an important wafer performance criterion, but they are widely recognized to be the cause of other types of device failures usually associated with current leakage problems.

The density of such vacancy and self-interstitial agglomerated defects in Czochralski silicon is conventionally within the range of about $1*10^3/cm^3$ to about $1*10^7/cm^3$. While these values are relatively low, agglomerated intrinsic point defects are of rapidly increasing importance to device manufacturers and, in fact, are now seen as yield-limiting factors in device fabrication processes.

One approach which has been suggested to control the formation of agglomerated defects is to control the initial concentration of the point defects when the single crystal silicon is formed upon solidification from a molten silicon mass by controlling the growth rate (v) of the single crystal silicon ingot from the molten silicon mass, wherein higher growth rates tend to produce vacancy rich material and lower growth rates tend to produce interstitial rich material, and controlling the axial temperature gradient, G, in the vicinity of the solid-liquid interface of the growing crystal for a given temperature gradient. In particular, it has been suggested that the radial variation of the axial temperature gradient be no greater than 5° C./cm. or less. See, e.g., Iida et al., EP0890662. This approach, however, requires rigorous design and control of the hot zone of a crystal puller.

Another approach which has been suggested to control the formation of agglomerated defects is to control the initial concentration of vacancy or interstitial point defects when the single crystal silicon is formed upon solidification from a molten silicon mass and controlling the cooling rate of the crystal from the temperature of solidification to a temperature of about 1,050° C. to permit the radial diffusion of silicon self-interstitial atoms or vacancies towards the lateral surface of the ingot or towards each other causing recombination thereby suppressing the concentration of intrinsic point defects to maintain the supersaturation of the vacancy system or the interstitial system at values which are less than those at which agglomeration reactions occur. See, for example, Falster et al., U.S. Pat. No. 5,919,302 and Falster et al., WO 98/45509. While these approaches may be successfully used to prepare single crystal silicon which is substantially free of agglomerated vacancy or interstitial defects, significant time may be required to allow for adequate diffusion of vacancies and interstitials. This may have the effect of reducing the throughput for the crystal puller.

SUMMARY OF THE INVENTION

Among the several objects and features of the present invention may be noted a process for producing a single crystal silicon ingot, a significant portion of which is substantially free of agglomerated intrinsic point defects which negatively impact the semiconductor properties of the silicon; the provision of a process for producing a single crystal silicon ingot having alternating regions of vacancy dominated and silicon self-interstitial dominated regions said silicon self-interstitial dominated regions being substantially free of agglomerated intrinsic point defects; the provision of such a process which does not substantially diminish the throughput of the crystal puller; the provision of such a process which substantially reduces the crystal puller from limitations on growth rate; the provision of such a process which substantial reduces the crystal puller from limitations on the average axial temperature gradient $G_o$; and the provision of a method for sorting the wafers sliced from said single crystal silicon ingot such that wafers which are substantially free of agglomerated intrinsic defects may be visually identified.

Briefly, therefore, the present invention is directed to a process for the preparation of a silicon single crystal ingot, a substantial portion of which is substantially free of agglomerated intrinsic point defects. The process comprising the controlling a growth velocity, v, and an average axial temperature gradient, $G_0$, such that the ratio of $v/G_0$ is varied to initially produce in the constant diameter portion of the ingot two or more regions, in which crystal lattice vacancies are the predominant intrinsic point defect, separated along the axis by one or more regions, in which silicon self-interstitial atoms are the predominant intrinsic point defect. The regions in which crystal lattice vacancies are initially the predominant intrinsic point defects have an axial length, $L_{vac.}$, and a radius, $R_{vac.}$, extending from the axis of the ingot towards the lateral surface which is at least about 10% of the radius, R, of the constant diameter portion of the crystal. The region(s) in which silicon self-interstitial atoms are initially the predominant intrinsic point defects have an axial length of $L_{int.}$ and extend across the entire radius, R, of the constant diameter portion of the silicon single crystal. The regions are cooled from the temperature of solidification at a rate which allows silicon self-interstitial atoms and vacancies from the regions to diffuse and recombine to reduce the concentration of silicon self-interstitial atoms in the region(s) in which silicon self-interstitial atoms were initially the predominant intrinsic point defect and to reduce the concentration of crystal lattice vacancies in the region(s) in which crystal lattice vacancies were initially the predominant intrinsic point defect.

The present invention is further directed to a process for the preparation of a silicon single, crystal ingot, a substantial portion of which is substantially free of agglomerated intrinsic point defects. The process comprising controlling a growth velocity, v, to initially produce in the constant diameter portion of the ingot two or more regions, in which crystal lattice vacancies are the predominant intrinsic point defect, separated along the axis by one or more regions, in which silicon self-interstitial atoms are the predominant intrinsic point defect. The regions in which crystal lattice vacancies are initially the predominant intrinsic point defects have an axial length, $L_{vac.}$, and a radius, $R_{vac.}$, extending from the axis of the ingot towards the lateral surface which is at least about 10% of the radius, R, of the constant diameter portion of the crystal. The region(s) in which silicon self-interstitial atoms are initially the predominant intrinsic point defects have an axial length of $L_{int.}$ and extend across the entire radius, R, of the constant diameter portion of the silicon single crystal. The regions are cooled from the temperature of solidification at a rate which allows silicon self-interstitial atoms and vacancies from the regions to diffuse and recombine to reduce the concentration of silicon self-interstitial atoms in the region(s) in which silicon self-interstitial atoms were initially the predominant intrinsic point defect and to reduce the concentration of crystal lattice vacancies in the region(s) in which crystal lattice vacancies were initially the predominant intrinsic point defect.

The present invention is further directed to a single crystal silicon ingot having a constant diameter portion comprising multiple axially symmetric regions alternating along the axis of the ingot between a region wherein vacancies are the predominant intrinsic point defect and a region wherein interstitials are the predominant intrinsic point defect, said ingot having at least 2 interstitial dominant regions which are substantially free of agglomerated interstitial defects separated by a vacancy dominant region along the axis of the constant diameter portion of the ingot Other objects and features of this invention will be in part apparent and in part pointed out hereinafter.

DETAILED DESCRIPTION OF THE PREFERRED EMBODIMENTS

Figure 1:
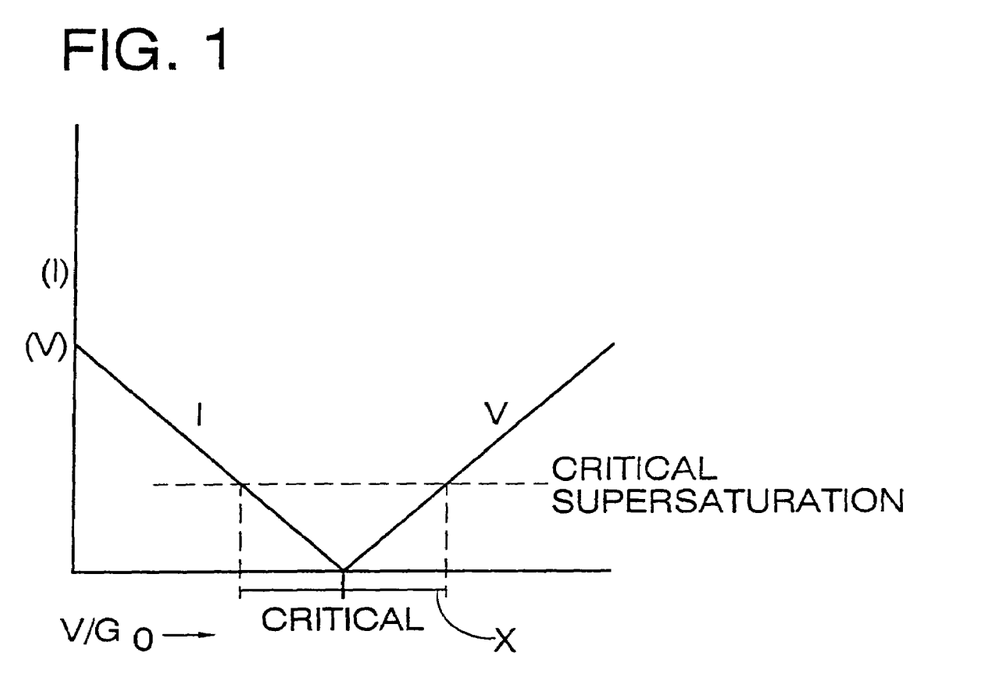
FIG. 1 is a graph which shows an example of how the initial concentration of self-interstitials, [I], and vacancies, [V], changes with an increase in the value of the ratio $v/G_0$, where v is the growth velocity and $G_0$ is the average axial temperature gradient.
Figure 2:
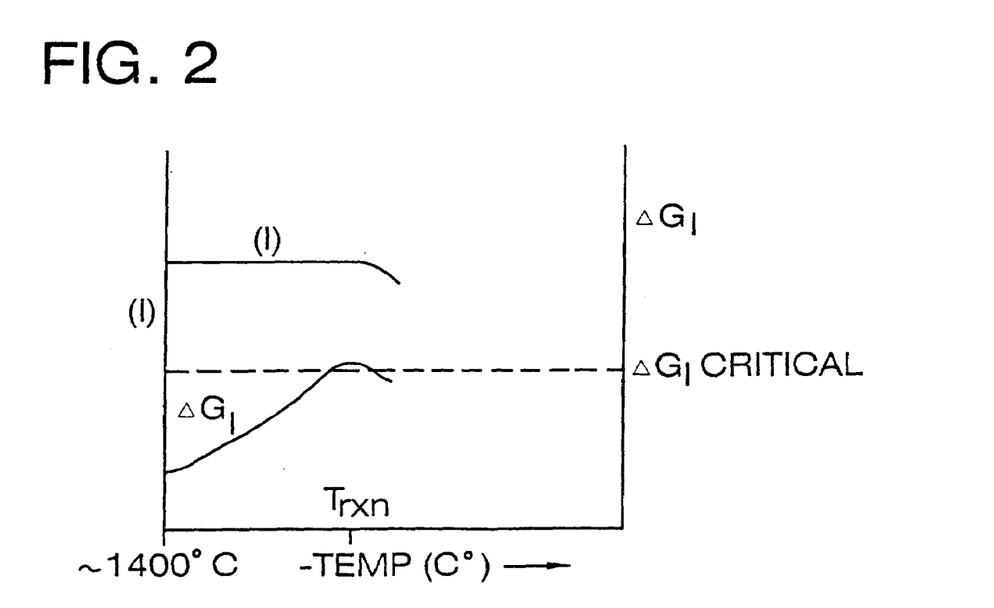
FIG. 2 is a graph which shows an example of how $\Delta G_I$, the change in free energy required for the formation of agglomerated interstitial defects, increases as the temperature, T, decreases, for a given initial concentration of self-interstitials, [I].
Figure 3:
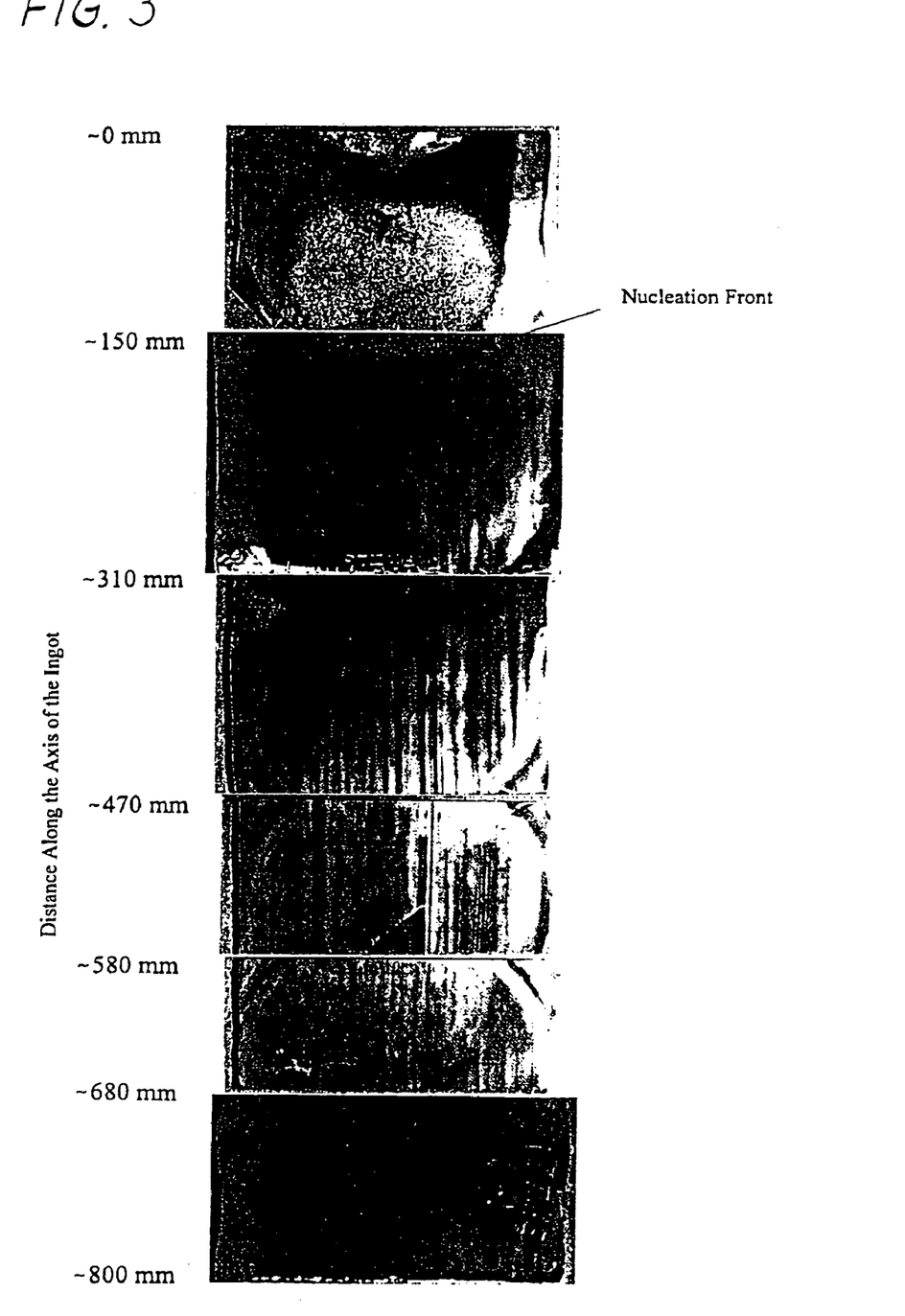
FIG. 3 is a cross-sectional image of an ingot prepared by quench cooling the ingot through the temperature range at which agglomerated intrinsic point defects nucleate.
Figure 4A:
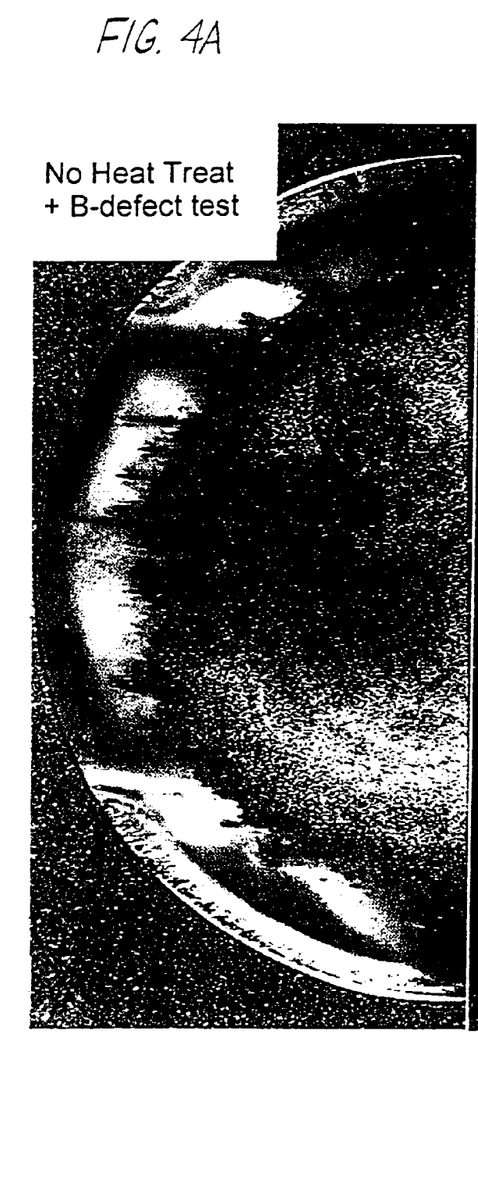
FIG. 4 is an image comparing a wafer having B-defects before being subjected to a B-defect annihilation heat-treatment to a wafer having B-defects which was subjected to a B-defect annihilation heat-treatment.
Figure 4B:
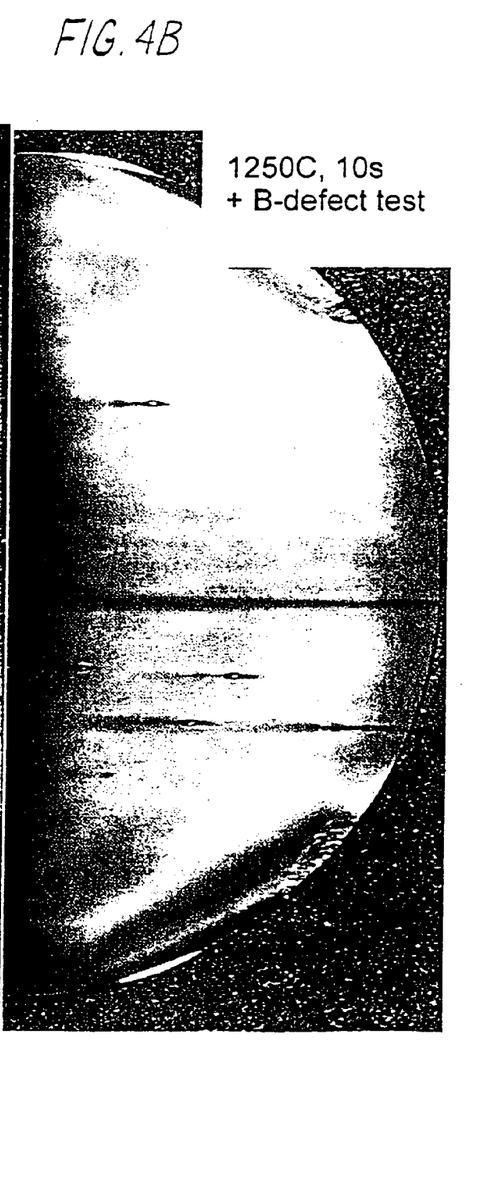

Based upon experimental evidence to date, the type and initial concentration of intrinsic point defects appears to be initially determined as the ingot cools from the temperature of solidification (i.e., about 1410° C.) to a temperature greater than 1300° C. (i.e., at least about 1325° C., at least about 1350° C. or even at least about 1375° C.). That is, the type and initial concentration of these defects are controlled by the ratio $v/G_0$, where v is the growth velocity and $G_0$ is the average axial temperature gradient over this temperature range.

The transition between vacancy and interstitial dominated material occurs at a critical value of $v/G_0$ which, based upon currently available information, appears to be about $2.1 \times 10^{-5}$ cm$^2$/sK where $G_0$ is determined under conditions in which the axial temperature gradient is constant within the temperature range defined above. At this critical value, the resulting concentrations of these intrinsic point defects are equal. If the value of $v/G_0$ exceeds the critical value, vacancies are the predominant intrinsic point defect and the concentration of vacancies increases with increasing $v/G_0$. If the value of $v/G_0$ is less than the critical value, silicon self-interstitials are the predominant intrinsic point defect and the concentration of silicon self-interstitials increases with decreasing $v/G_0$.

The ratio of $v/G_0$, and therefore the type of intrinsic point defect initially predominant in a particular region may be controlled by controlling the temperature gradient, $G_0$, the growth rate v, or by controlling both $G_0$ and v. Preferably, however, the ratio of $v/G_0$ is controlled by controlling the growth rate v. For a given $G_0$, therefore, a decrease in the growth rate, v, tends to increase the concentration of silicon self-interstitials and an increase in the growth rate, v, tends to increase the concentration of vacancies.

Once the initial concentration of an intrinsic point defects is established, the formation of agglomerated defects is thought to be dependent upon the free energy of the system. For a given concentration of intrinsic point defects a decrease in temperature yields an increase in the change in free energy for the reaction which forms agglomerated defects from the intrinsic point defects. Thus, as a region containing a concentration of vacancies or interstitials cools from the temperature of solidification through the temperature at which agglomerated defects are nucleated, the energy barrier for the formation of agglomerated vacancy or interstitial defects is approached. As cooling continues, this energy barrier may eventually be exceeded, at which point an agglomeration reaction occurs (See, e.g., Falster et al., U.S. Pat. No. 5,919,302 and Falster et al., WO 98/45509).

The temperature at which nucleation of agglomerated defects occurs, i.e. the temperature of agglomeration, $T_A$, is dependent upon the concentration and type of predominant intrinsic point defects (vacancy or silicon self-interstitial). In general, the temperature of agglomeration, $T_A$, increases with increasing concentration of intrinsic point defect. In addition, the range of nucleation temperatures for agglomerated vacancy-type defects is somewhat greater than the range of nucleation temperatures for agglomerated interstitial-type defects; stated another way, over the range of vacancy concentrations typically produced in Czochralski grown single crystal silicon the temperature of agglomeration, $T_A$, for agglomerated vacancy defects is generally between about 1,000° C. and about 1,200° C. and typically between about 1,000° C. and about 1,100° C. whereas over the range of silicon self-interstitial concentrations typically produced in Czochralski grown single crystal silicon, the temperature of agglomeration, $T_A$, is generally between about 850° C. and about 1,100° C. and typically between about 870° C. and about 970° C.

The concentration of vacancies or interstitials may be suppressed, however by allowing the ingot to remain above the temperature of agglomeration, $T_A$, for a time period sufficient to allow the vacancies or interstitials to diffuse radially to the surface of the ingot. However, large diameter ingots require substantial time periods for vacancies or interstitials located at the axis of the ingot to diffuse to the surface.

Ingots comprising concentrically positioned regions of vacancies and regions of interstitials, provide an additional mechanism for reducing the concentration of vacancies and interstitials, wherein the ingot may be maintained above the temperature of agglomeration, $T_A$, for a time period sufficient to allow the vacancies and interstitials to diffuse radially towards each other such that they recombine and are mutually annihilated.

In accordance with the present invention, at least a significant fraction of the constant diameter portion of the ingot may be grown substantially free of agglomerated intrinsic point defects by controlling the growth conditions to initially produce in the constant diameter portion of the ingot, separated regions along the axis having alternating predominant intrinsic point defects. Stated another way, the predominant intrinsic point defect alternates between vacancy dominated regions and silicon self-interstitial dominated regions along the axis of the constant diameter portion of the ingot. As a result, vacancies and interstitials located near the axis may diffuse axially towards each other and recombine while intrinsic point defects near the lateral surface can diffuse radially towards the surface, thus utilizing both radial and axial diffusion to suppress the concentration of intrinsic point defects. Because interstitials diffuse at much faster rates than vacancies, the interstitials will travel a much further distance than the vacancies prior to the recombination. As a practical matter, therefore, it is preferred that the constant diameter portion of the ingot initially comprise relatively larger regions of silicon self-interstitial dominated regions separated by relatively smaller vacancy dominated regions having a high concentration of vacancies. The vacancy dominated regions thus serve as sinks for the rapidly diffusing silicon self interstitials where they are annihilated to suppress the concentration of silicon self-interstitials prior to cooling below the temperature of agglomeration.

Without being held to a particular theory, it is believed that, the out-diffusion of silicon self interstitials from an interstitial dominated region located axially between two vacancy dominated regions may be described by modeling the concentration field of interstitials. Accordingly, the concentration of interstitials can be described by as a function of time by expanding the interstitial concentration field $C_i$ (r,z,t) into a series of eigenfunctions wherein each such function is a product of the Bessel function $J_o(\lambda r/R)$ for the radial concentration profile and of the sinusoidal function $\sin(\mu z/L)$ for the axial concentration profile and wherein $\lambda$ and $\mu$ are the roots of those two functions, at a distance (r) equal to the radius (R) of the region, and at a distance (z) along the axis equal to the length (L) of the region. Deep decay in the concentration implies that only the first term of the series is relevant such that:

$$C_i/C_m = A\, J_o(\lambda r/R)\sin(\pi z/L)\exp(-t/\tau) \qquad (2)$$

with $\lambda=2.4048$, wherein $C_m$ is the melting point equilibrium concentration and the ratio $C_i/C_m$ represents the normalized interstitial concentration. The decay time $\tau$ is expressed through the two eigenvalues, $\lambda/R$ and $\pi/L$ such that:

$$1/\tau = D[(\lambda/R)^2 + (\pi/L)^2] \qquad (3)$$

wherein D is the diffusion coefficient for silicon-self interstitials

The expansion coefficient A in equation (2) is expressed through the imprinted interstitial concentration $C_{imp}=B(1-V/V_{cr})$, where B is about 0.5 such that:

$$A = 2.04 B(1 - V/V_{cr}) \qquad (4)$$

where the coefficient 2.04 is the product of the radial expansion coefficient 1.602 and the axial expansion coefficient $4/\pi=1.27$, v is the growth velocity and $V_{cr}$ is the critical growth velocity.

Furthermore, a relationship exists between the growth velocity, the time the ingot dwells above the temperature of agglomeration, $T_A$, and the dwell length, $L_{dw}$, corresponding to the distance over which a given axial position travels as the ingot cools from near the solidification temperature to $T_A$. The relationship between this distance, or "dwell length" ($L_{dw}$), the growth velocity, v, and the dwell time, $t_{dw}$, is expressed as follows:

$$t_{dw} = L_{dw}/v \qquad (5)$$

To prevent the formation of agglomerated intrinsic point defects, the dwell time, $t_{dw}$, is preferably of sufficient duration to allow enough interstitials or vacancies to diffuse and be annihilated to sufficiently suppress the concentration thus preventing the formation of agglomerated intrinsic point defects as that portion of the ingot exceeds the dwell length and cools below the temperature of agglomeration.

The temperature profile in the hot zone of the crystal grower is believed to be almost unaffected by variations in the growth velocity, v, such that the dwell length, $L_{dw}$, may be considered as a constant for a given hot zone. Thus, the hot zone can be designed to provide the dwell length required to provide a sufficient dwell time based on a desired set of growth conditions, for example, the crystal diameter and growth rate.

Under steady growth processes, (ie. processes wherein the growth rate is controlled to produce an ingot which is predominantly interstitial rich or vacancy rich from center to edge throughout the growth of the ingot) there exists a relationship between the dwell length, $L_{dw}$, the critical growth rate, $V_{cr}$, and the radius of the ingot, R, wherein for a given ingot radius and critical growth rate, there exist a dwell length that will provide sufficient dwell time, $t_{dw}$, above the agglomeration temperature for the intrinsic point defects to diffuse to the surface of the ingot, suppressing the concentration and preventing the formation of agglomerated intrinsic point defects. The relationship is expressed as follows:

$$L_{dw} = 0.35 V_{cr} R^2 \quad (6)$$

The same requirement is applicable to ingots having a segment wherein the predominant intrinsic point defect alternates along the axis of the ingot between regions wherein vacancies are the predominant intrinsic point defect and regions wherein silicon self-interstitials are the predominant intrinsic point defect. Provided the quantity of vacancies in the vacancy dominated regions is at least about the quantity of interstitials in the interstitial dominated region to allow for recombination, there will exist an additional mechanism for suppressing the concentration, i.e., axial diffusion and recombination. Accordingly, the concentration of interstitials will be suppressed faster than an ingot relying predominantly on radial diffusion. Stated differently, silicon-self interstitials in an interstitial dominated region having a radius equal to the radius, R, of the ingot and having vacancy dominated regions located along the axis of the ingot before and after the interstitial dominated region, will diffuse from the region both axially and radially causing the concentration of silicon-self interstitials to be suppressed at a faster rate. That is, because the silicon-self interstitials near the axis can diffuse axially to the vacancy dominated regions, the maximum length in which any silicon-self interstitial is required to travel before recombining and being eliminated is significantly reduced. To describe the diffusion rates and suppression of the interstitial concentration, the region can be characterized as having an effective radius, $R_{eff}$, less than the actual radius, R of the ingot. The effective radius, $R_{eff}$, is generally less than the crystal radius and may be expressed a function of the ingot radius, R, and the axial length of the interstitial dominated region, bound along the axis in the core region radially near and including the axis, by vacancy dominated regions, as follows:

$$R_{eff} = R/[1+(\pi R/\lambda L)^2]^{1/2} \quad (7)$$

Thus, by substituting the effective radius, $R_{eff}$, for R in equation (6), the required dwell length to prevent the agglomeration of intrinsic point defects may be determined.

For a considerable gain in the growth and cooling rate therefore, the length, $L_{int.}$, of an interstitial region, having a vacancy region both before and after the interstitial region along the axis of the ingot, is preferably comparable to about twice the radius R (or less), such that $R_{eff}$ becomes less than R, thus reducing the required dwell length according to equations (6) and (7) and correspondingly reducing the required dwell time, $t_{dw}$, according to equation (5). Thus, an effective dwell time, $t_{dw\text{-}eff}$, can be achieved which is less than about 85%, less than about 60%, less than about 40%, and even less than about 20% of the dwell time that would otherwise be required if the silicon self-interstitial atoms were to diffuse primarily in the radial direction without the benefit of axial diffusion to suppress the concentration of silicon self-interstitial atoms.

To prevent the formation of agglomerated intrinsic point defects in interstitial dominant regions, the normalized concentration of interstitials, $C_i/C_m$ is preferably suppressed below some critical value, $(C_i/C_m)_{cr}$ (equal to about 0.01 at $T_A = 920°$ C.). It follows from equations (2) through (4), that to suppress $C_i/C_m$ below the critical level of $(C_i/C_m)_{cr} = 0.01$ (at $T_A = 920°$ C.) the dwell time $t_{dw}$ is preferably long enough, to fulfill the condition:

$$Dt_{dw}[(\lambda/R)^2 + (p/L)^2] > \log[(1-V/V_{cr})/(C_i/C_m)_{cr}]. \quad (8)$$

Accordingly, if the dwell time is specified (by a particular hot zone) then the required value of the length, $L_{int.}$, of the silicon self-interstitial dominant region may be determined from equation (8) for a growth rate ratio, $V/V_{cr}$, producing a silicon self-interstitial dominant region. For example, given a $V/V_{cr}$ ratio of about 0.9, the right-hand part of equation (8) becomes about 1. Therefore, by knowing the radius, R, of the ingot and the dwell time, $t_{dw}$, of the crystal grower, the length, $L_{int.}$, of an interstitial dominant region may be determined such that the concentration of interstitials will be suppressed below the critical level of $(C_i/C_m)_{cr} = 0.01$ (at $T_A = 920°$ C.) within the dwell time specified by the hot zone.

Ideally, the initial concentrations of vacancies in the vacancy dominant regions are sufficient to recombine with the silicon self interstitials, with the resulting vacancy concentrations being sufficiently suppressed to prevent agglomerated vacancies from forming as the ingot cools. However, because the vacancies diffuse at rates substantially slower than silicon self-interstitials, as a practical matter, the concentration of the vacancy dominated region may not be suppressed sufficiently to prevent agglomerated vacancies. Furthermore, it is preferable that the vacancy dominated regions contain an excess of vacancies over the quantity of vacancies required to combine with and annihilate silicon self interstitials to suppress the concentration of silicon self-interstitials. This excess may result in agglomerated vacancies upon cooling below the agglomeration temperature.

The concentrations of vacancies and interstitials in each region are proportional to the growth rate ratios, $(V/V_{cr})_{vacancy}$ and $V/V_{cr})_{interstitial}$. Accordingly, the minimum length ratio for the vacancy dominated region to the interstitial dominated region required to provide a quantity of vacancies equal to the number of silicon self interstitials, may be expressed in relation to the normalized growth rate ratio such that:

$$[L_{vacancy}/L_{interstitial}]_{min} = 0.37[(V/V_{cr})_{interstitial}/(V/V_{cr})_{vacancy}] \quad (9)$$

The growth rate during the formation of the vacancy regions may be any growth rate in excess of the critical growth rate without departing from the scope of the invention. It is to be noted, however, that as the growth rate decreases, approaching the critical growth rate, i.e. the closer $(V/V_{cr})_{vacancy}$ gets to 1, the concentration of vacancies and typically the radius of the vacancy dominated region decreases, decreasing the total quantity of vacancies available for recombination. According to equation (9), therefore, decreases in $(V/V_{cr})_{vacancy}$ causes increases in the required length of the vacancy dominated regions relative to the length of silicon self-interstitial region. Correspondingly, as the growth rate increases, the concentration of vacancies and typically the diameter of the vacancy dominated region increases, increasing the total quantity of vacancies available for recombination, thus decreasing the required length of the vacancy dominated regions relative to the length of silicon self-interstitial dominated region. Preferably, therefore, the growth velocity is controlled during the formation of the vacancy dominated regions, such that the ratio $(V/V_{cr})_{vacancy}$ is at least about 1.5, more preferably at least about 2.0, more preferably at least about 2.5 and may even be at least about 3.5 or greater depending on the particular hot zone design.

Conversely, as the growth velocity in the silicon self-interstitial region becomes closer to the critical growth velocity, i.e., the ratio $(V/V_{cr})_{interstitial}$ is increased, the concentration of silicon self-interstitials is reduced and, according to equation (9), $[L_{vac.}/L_{int.}]_{min}$ is reduced. Preferably, during the growth of the silicon self-interstitial region, the growth velocity is controlled such that the ratio $(V/V_{cr})_{interstitial}$ is from about 0.5 to about 0.95, more preferably from about 0.7 to about 0.9, and most preferably from about 0.8 to about 0.9. Although slower growth velocities may be utilized without departing from the scope of the invention, as a practical matter, reduced growth velocities decrease the throughput of the crystal growth process and therefore are not desirable. Additionally, as the growth velocity is decrease further below the critical growth velocity, the total quantity of silicon-self interstitials increases.

Preferably the vacancy dominated regions are as short as possible, with a greater total volume of the constant diameter portion of the ingot preferably being grown as silicon self-interstitial dominant material to improve the overall yield of substantially defect-free silicon. However, it is also preferred that the total number of vacancies is at least about as much as the total number of silicon self-interstitials. Thus, it is preferred that the growth velocity is cycled asymmetrically about the critical growth velocity. That is, it is preferred that the growth velocity is increased to at least about 150 percent and as much as 350 percent of the critical growth rate during the formation of the vacancy dominated region while preferably being reduced to only about 90 percent of the critical growth rate during the formation of the interstitial dominated region.

Because interstitials diffuse faster than vacancies, the interface between the interstitial dominant region and the vacancy dominated regions will shift causing the resulting interstitial dominant region, substantially free of agglomerated intrinsic point defects to have an axial length somewhat greater than $L_{int.}$. Preferably, the number of vacancies in the vacancy dominant region is in excess of the quantity of silicon self-interstitials in the interstitial dominant region. Accordingly, the length ratio, $[L_{vac.}/L_{int.}]$ may be selected at some value greater than the minimum for a given set of growth velocities to provide an excess of vacancies.

In general, a silicon-single crystal may be grown by the Czochralski method to form an ingot having a central axis, a seed-cone, an end-cone, a constant diameter portion between the seed-cone and the end-cone having a lateral surface, and a radius, R, extending from the central axis to the lateral surface. The radius, R, of the constant diameter portion of the ingot is preferably at least about 75 mm, at least about 100 mm and may even be at least about 150 mm or greater and has an axial length, L, of at least about 400 mm, at least about 600 mm, and may even be at least about 1000 mm or greater.

In accordance with the present invention, the ratio of the growth velocity over the average axial temperature gradient, $v/G_0$, is controlled to initially produced in the constant diameter portion of the ingot two or more regions, in which crystal lattice vacancies are the predominant intrinsic point defect, separated along the axis by one or more regions, in which silicon self-interstitial atoms are the predominant intrinsic point defect by intentionally varying the ratio $v/G_0$. In a preferred embodiment, the ratio is controlled by varying the growth velocity as discussed above.

In particular, the growth velocity is controlled such that the region or regions in which silicon self-interstitial atoms are the predominant intrinsic point defect have an axial length of $L_{int.}$ which is less than twice the radius of the constant diameter portion of the ingot and has a radius $R_{int.}$ which extends across the entire radius, R, of the constant diameter portion of the ingot to take advantage of the axial diffusion and recombination of intrinsic point defects in the near axis region of the ingot. It is preferred that the ingot is grown under conditions in which a substantial portion of the ingot comprises a region or regions in which silicon self-interstitial atoms are the predominant intrinsic point defects. Preferably, therefore, the axial length of the interstitial dominant regions, $L_{int.}$, is at least about 25% of the radius of the constant diameter portion of the ingot.

Preferably, therefore, the axial length, $L_{int.}$, of the interstitial dominant region is at least about 25% and less than about 2R, at least about 50% and less about than about 1.5R, and preferably about equal to the radius, R, of the constant diameter portion of the ingot. The axial length, $L_{int.}$, of the interstitial dominant region may exceed 2R or be less than 25% of R, however regions having an axial length greater than 2R will have increase diffusion times required to suppress the concentration of interstitials relying increasingly on radial diffusion from the axis to the lateral surface, and regions having an axial length less than 25% may reduce the total volume of substantially defect free silicon in the ingot.

The growth rate is further controlled such that the regions in which crystal lattice vacancies are initially the predominant intrinsic point defects have a radius, $R_{vac.}$, extending from the axis of the ingot towards the lateral surface which is at least about 10%, at least about 50%, and at least about 90% or greater of the radius, R, of the constant diameter portion of the crystal. The initial axial length, $L_{vac.}$, of the vacancy dominated regions is preferably at least about 0.05 times the initial axial length, $L_{int.}$, of the interstitial dominated regions and may be at least about 0.1, or even at least about 0.5 times the initial axial length, $L_{int.}$, of the interstitial dominated regions, depending on the ratio between the normalized growth rate for the vacancy dominated regions and the normalized growth rate of the interstitial dominated regions as described in equation (9). For example, if $V_{vac.}$ is 1.5 times $V_{cr}$ and $V_{int.}$ is 0.9 times $V_{cr}$ then $(L_{vac.}/L_{int.})$ is preferably at least about 0.22. Similarly, if $V_{vac.}$ is 2 times $V_{cr}$ and $V_{int.}$ is 0.9 times $V_{cr}$ then $(L_{vac.}/L_{int.})$ is preferably at least about 0.17; if $V_{vac.}$ is 2.5 times $V_{cr}$ and $V_{int.}$ is 0.9 times $V_{cr}$ then $(L_{vac.}/L_{int.})$ is preferably at least about 0.14; if $V_{vac.}$ is 1.5 times $V_{cr}$ and $V_{int.}$ is 0.5 times $V_{cr}$ then ($L_{vac.}/L_{int.}$) is preferably at least about 0.12; if $V_{vac.}$ is 2 times $V_{cr}$ and $V_{int.}$ is 0.5 times $V_{cr}$ then ($L_{vac.}/L_{int.}$) is preferably at least about 0.1; and, if $V_{vac.}$ is 2.5 times $V_{cr}$ and $V_{int.}$ is 0.5 times $V_{cr}$ then ($L_{vac.}/L_{int.}$) is preferably at least about 0.08.

Thus, according to the process of the present invention, the growth rate is preferably controlled to initially produce in the constant diameter portion of the ingot at least about 2 vacancy dominated regions separated along the axial direction by at least 1 interstitial dominated regions. More preferably, the growth rate is controlled to initially produce in the constant diameter portion of the ingot, at least about 4, 6, 10, and even as many as 16 or greater vacancy dominated regions separated along the axis by one or more interstitial dominated region(s).

As noted above, the radius of the vacancy dominated region(s) may be less than the radius of the constant diameter portion of the ingot. Additionally, vacancy dominated regions having a radius less than the radius of the constant diameter portion of the ingot, will generally have a silicon self-interstitial dominated region extending radially inward from the lateral surface of the ingot to the vacancy dominated region. Thus, multiple vacancy dominated regions may be separated along the axis of the ingot by a single continuous interstitial dominated region, having a radius that varies from a minimum approximately equal to the difference between the radius of the vacancy dominated region and the radius of the constant diameter portion of the ingot to a maximum equal to the radius of the constant diameter portion of the ingot. For example, several vacancy dominated regions each having a radius equal to 10% of the radius of the constant diameter portion of the ingot may be separated along the axis of the ingot by a single continuous interstitial dominated region, having a radius which varies between 90% and 100% of the radius of the constant diameter portion of the ingot, wherein the vacancy dominated regions are separated along the axis when the interstitial dominated region has a radius equal to 100% of the radius of the constant diameter portion of the ingot. Alternatively, multiple vacancy dominated regions having a radius equal to the radius of the constant diameter portion of the ingot may be separated along the axis of the ingot by multiple interstitial dominated regions each having a radius equal to the constant diameter portion of the ingot.

Therefore, according to the process of the present invention, the growth rate is preferably controlled to initially form in the ingot one or more interstitially dominated regions separated along the axis by the vacancy dominated regions referred to above, wherein the interstitial dominated region(s) may be discontinuous regions completely separated along the axis by multiple vacancy regions having a radius equal to the constant diameter portion of the ingot, or one or more continuous region(s) separate along the axis by multiple vacancy regions having a radius less than the radius of the constant diameter portion of the ingot. Thus, according to the present invention, the growth rate is controlled to initially form 1 or more interstitially dominated regions having at least one vacancy dominated region axially adjacent to the interstitially dominated region(s), the vacancy dominated regions serving as a sink to which silicon self-interstitials near the axis may diffuse and be annihilated.

The interstitial dominated regions are then cooled from the temperature of solidification at a rate which allows silicon self-interstitial atoms and vacancies from the regions to diffuse both radially and axially such that a sufficient number of silicon self-interstitial atoms recombine with vacancies to reduce the concentration of silicon self-interstitial atoms in the region(s) in which silicon self-interstitial atoms were initially the predominant intrinsic point defect and to reduce the concentration of crystal lattice vacancies in the region(s) in which crystal lattice vacancies were initially the predominant intrinsic point defect. Preferably, the regions are maintained at a temperature above $T_A$ for a time period of at least an effective dwell time, $t_{dw\text{-}eff}$, required to allow a sufficient quantity of silicon self-interstitial atoms to diffuse to the surface of the ingot and to the vacancy dominated region(s) to suppress the concentration of silicon self-interstitial atoms in the region(s) in which silicon self-interstitial atoms were initially the predominant intrinsic point defect below a critical concentration required for agglomerated intrinsic point defects to nucleate.

Once the concentration of interstitials in the region have been suppressed, the region may be cooled such that a significant portion of the resulting ingot is substantially free of any agglomerated intrinsic point defects.

Depending upon the resulting concentration and distribution of vacancies and self-interstitial atoms in the various regions of the ingot, the formation of agglomerated intrinsic point defects may thereafter be avoided by controlling the diffusion of the intrinsic point defects and/or by quench cooling the ingot. Thus, if the resulting concentration of vacancies or silicon self-interstitials is below the concentration at which vacancies or silicon self-interstitials may agglomerate upon cooling, the region may be allowed to cool by the standard Czochralski process. If, however the vacancy or interstitial dominated regions or portions thereof have vacancy or interstitial concentrations greater than the concentration at which the interstitials or vacancies may agglomerate upon cooling, the cooling rate of the region may be controlled such that additional time is allowed for silicon self-interstitials and/or vacancies to diffuse radially to the lateral surface of the ingot and/or diffuse towards and recombine with each other further suppressing the concentration of vacancies and/or silicon self-interstitials during cooling such that the resulting ingot is substantially free of agglomerated intrinsic point defects (See for example co-pending U.S. patent application Ser. Nos. 09/344,036 and 09/344,709, both incorporated herein by reference.) Additionally, if the concentration of vacancies or silicon self-interstitials is greater than the concentration at which the vacancies or silicon self-interstitials may agglomerate upon cooling, the ingot or portions thereof may be quench cooled such that the vacancies or silicon self-interstitials are effectively frozen in position without allowing sufficient time for them to agglomerate, such that the resulting ingot is substantially free of agglomerated intrinsic point defects as described in U.S. application Ser. No. 09/661,745 claiming priority from Provisional Application No. 60/155,725 incorporated herein by reference.

Alternatively, the concentration of interstitials in the interstitial dominated region(s) may only be suppressed such that upon cooling, the region(s) contain some agglomerated interstitial type defects, wherein the agglomerated interstitial-type defects are B-type defects only.

In general, control of the average axial temperature gradient, $G_0$, may be achieved primarily through the design of the "hot zone" of the crystal puller, i.e. the graphite (or other materials) that makes up the heater, insulation, heat and radiation shields, among other things. Although the design particulars may vary depending upon the make and model of the crystal puller, in general, $G_0$ may be controlled using any of the means currently known in the art for controlling heat transfer at the melt/solid interface, including reflectors, radiation shields, purge tubes, light pipes, and heaters. In general, radial variations in $G_0$ are minimized by positioning such an apparatus within about one crystal diameter above the melt/solid interface. $G_0$ can be controlled further by adjusting the position of the apparatus relative to the melt and crystal. This is accomplished either by adjusting the position of the apparatus in the hot zone, or by adjusting the position of the melt surface in the hot zone. In addition, when a heater is employed, $G_0$ may be further controlled by adjusting the power supplied to the heater. Any, or all, of these methods can be used during a batch Czochralski process in which melt volume is depleted during the process.

Varying the growth rate during the growth of the portion of ingot typically referred to as the constant diameter portion, i.e. the portion between the seed cone and the end cone, typically causes variations in the diameter along the axis. That is, the diameter of vacancy dominated regions is less than the diameter of interstitial dominated regions. As such, wafers sliced from the ingot having reduced diameters will typically be vacancy dominated; wafers sliced from the ingot having increased diameters will typically be interstitial dominated. Accordingly, the diameter of the ingot and subsequently the diameter of wafers sliced from the ingot may be used to sort the resulting wafers between those wafers having vacancies as the predominant intrinsic point defect, and those wafers having silicon self-interstitials as the predominant intrinsic point defect.

DEFINITIONS

It is to be noted that, as used herein, the following phrases shall have the given meanings: "agglomerated intrinsic point defects" shall mean defects caused (i) by the reaction in which vacancies agglomerate or (ii) by the reaction in which self-interstitials agglomerate; "agglomerated vacancy defects" shall mean agglomerated vacancy point defects caused by the reaction in which crystal lattice vacancies agglomerate, examples include D-defects, flow pattern defects, gate oxide integrity defects, crystal originated particle defects, and crystal originated light point defects; "agglomerated interstitial defects" shall mean agglomerated intrinsic point defects caused by the reaction in which silicon self-interstitial atoms agglomerate to form A-defects (including dislocation loops and networks) and B-defects; "B-defects" shall mean agglomerated interstitial defects which are smaller than A-defect and which are capable of being dissolved if subjected to a heat treatment; "radius" shall mean the distance measured from a central axis to a circumferential edge of a single crystal silicon sample, such as a wafer, or an ingot slug or slab; "substantially free of agglomerated intrinsic point defects" shall mean a concentration of agglomerated defects which is less than the detection limit of these defects, which is currently about $10^4$ defects/cm$^3$; "vacancy dominated" and "self-interstitial dominated" shall mean material in which the intrinsic point defects are predominantly vacancies or self-interstitials, respectively; and, "visual detection of agglomerated intrinsic point defects," as well as variations thereof, shall refer to the detection of such defects using the naked eye under ordinary incandescent or fluorescent light sources, or optionally collimated or other enhanced light sources, and without the use of any instrumentation which would otherwise aid in defect detection or result in defect magnification, such as optical or infrared microscopy, X-ray diffraction, or laser scattering.

Detection of Agglomerated Defects

Agglomerated defects may be detected by a number of different techniques. For example, flow pattern defects, or D-defects, are typically detected by preferentially etching the single crystal silicon sample in a Secco etch solution for about 30 minutes, and then subjecting the sample to microscopic inspection. (see, e.g., H. Yamagishi et al., Semicond. Sci. Technol. 7, A135 (1992)). Although standard for the detection of agglomerated vacancy defects, this process may also be used to detect A-defects. When this technique is used, such defects appear as large pits on the surface of the sample when present.

Additionally, agglomerated intrinsic point defects may be visually detected by decorating these defects with a metal capable of diffusing into the single crystal silicon matrix upon the application of heat. Specifically, single crystal silicon samples, such as wafers, slugs or slabs, may be visually inspected for the presence of such defects by first coating a surface of the sample with a composition containing a metal capable of decorating these defects, such as a concentrated solution of copper nitrate. The coated sample is then heated to a temperature between about 900° C. and about 1000° C. for about 5 minutes to about 15 minutes in order to diffuse the metal into the sample. The heat treated sample is then cooled to room temperature, thus causing the metal to become critically supersaturated and precipitate at sites within the sample matrix at which defects are present.

After cooling, the sample is first subjected to a non-defect delineating etch, in order to remove surface residue and precipitants, by treating the sample with a bright etch solution for about 8 to about 12 minutes. A typical bright etch solution comprises about 55 percent nitric acid (70% solution by weight), about 20 percent hydrofluoric acid (49% solution by weight), and about 25 percent hydrochloric acid (concentrated solution).

The sample is then rinsed with deionized water and subjected to a second etching step by immersing the sample in, or treating it with, a Secco or Wright etch solution for about 35 to about 55 minutes. Typically, the sample will be etched using a Secco etch solution comprising about a 1:2 ratio of 0.15 M potassium dichromate and hydrofluoric acid (49% solution by weight). This etching step acts to reveal, or delineate, agglomerated defects which may be present.

In an alternative embodiment of this "defect decoration" process, the single crystal silicon sample is subjected to a thermal anneal prior to the application of the metal-containing composition. Typically, the sample is heated to a temperature ranging from about 850° C. to about 950° C. for about 3 hours to about 5 hours. This embodiment is particularly preferred for purposes of detecting B-type silicon self-interstitial agglomerated defects. Without being held to a particular theory, it is generally believed that this thermal treatment acts to stabilize and grow B-defects, such that they may be more easily decorated and detected.

Agglomerated vacancy defects may also be detected using laser scattering techniques, such as laser scattering tomography, which typically have a lower defect density detection limit that other etching techniques.

In general, regions of interstitial and vacancy dominated material free of agglomerated defects can be distinguished from each other and from material containing agglomerated defects by the copper decoration technique described above. Regions of defect-free interstitial dominated material contain no decorated features revealed by the etching whereas regions of defect-free vacancy dominated material (prior to a high-temperature oxygen nuclei dissolution treatment as described above) contain small etch pits due to copper decoration of the oxygen nuclei.

In view of the above, it will be seen that the several objects of the invention are achieved. As various changes could be made in the above-described process without departing from the scope of the invention, it is intended that all matters contained in the above description be interpreted as illustrative and not in a limiting sense. In addition, when introducing elements of the present invention or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

What is claimed is:

1. A process for the preparation of a silicon single crystal in which molten silicon is solidified into a crystal in accordance with the Czochralski method to form an ingot having a central axis, a seed-cone, an end-cone, a constant diameter portion between the seed-cone and the end-cone having a lateral surface, and a radius, R, extending from the central axis to the lateral surface of at least about 75 mm, the constant diameter portion having an axial length, L, the process comprising;

controlling a ratio, $v/G_0$, wherein, v is a growth velocity and, $G_0$ is an average axial temperature gradient over the temperature range from solidification to a temperature of no less than about 1325° C., during the growth of the constant diameter portion of the crystal, to initially produce in the constant diameter portion of the ingot a series of predominant intrinsic point defects alternating along the axis, the series comprising $N_{vac.}$ vacancy dominated regions and $N_{int.}$ silicon self interstitial dominated regions, wherein $N_{vac.}$ is at least 2 and $N_{int.}$ is at least 1, the vacancy dominated regions each having an axial length, $L_{vac.}$, and a radius, $R_{vac.}$, extending from the axis of the ingot towards the lateral surface which is at least about 10% of the radius, R, of the constant diameter portion of the crystal, the silicon self-interstitial dominated region(s) each having an axial length, $L_{int.}$, and a radial width which is equal to the radius, R, of the constant diameter portion of the silicon single crystal;

cooling said regions from the temperature of solidification at a rate which allows silicon self-interstitial atoms to diffuse radially to the lateral surface and to diffuse axially to vacancy dominated regions to reduce the concentration of silicon self-interstitial atoms in the region(s) in which silicon self-interstitial atoms were initially the predominant intrinsic point defect and to reduce the concentration of crystal lattice vacancies in the region(s) in which crystal lattice vacancies were initially the predominant intrinsic point defect.

2. The process of claim 1 wherein the ratio, $v/G_0$, is controlled by controlling the growth velocity, v.

3. The process of claim 2 wherein the growth velocity is controlled such that the growth velocity during the formation of the vacancy dominated region, $v_{vac.}$, is at least about 1.5 times a critical value, $V_{crit.}$, and the growth velocity during the formation of the interstitial dominated region, $V_{int.}$, is less than about 0.9 times the critical value $V_{crit.}$.

4. The process of claim 3 wherein the ratio of $L_{vac.}/L_{int.}$ is at least about 0.23.

5. The process of claim 3 wherein $V_{vac.}$ is at least about 2 times the critical value, $V_{crit.}$, during the growth of the vacancy dominated regions.

6. The process of claim 3 wherein the ratio of $L_{vac.}/L_{int.}$ is at least about 0.17.

7. The process of claim 3 wherein $v_{vac.}$ is at least about 2.5 times the critical value, $v_{crit.}$, during the growth of the vacancy dominated regions.

8. The process of claim 7 wherein the ratio of $L_{vac.}/L_{int.}$ is at least about 0.14.

9. The process of claim 2 wherein growth velocity is controlled such that the growth velocity during the formation of the vacancy dominated region, $v_{vac.}$, is at least about 1.5 times a critical value, $v_{crit.}$, and the growth velocity during the formation of the interstitial dominated region, $v_{int.}$, is less than about 0.5 times the critical value $v_{crit.}$.

10. The process of claim 9 wherein the ratio of $L_{vac.}/L_{int.}$ is at least about 0.12.

11. The process of claim 9 wherein $v_{vac.}$ is at least about 2 times the critical value, $v_{crit.}$, during the growth of the vacancy dominated regions.

12. The process of claim 11 wherein the ratio of $L_{vac.}/L_{int.}$ is at least about 0.1.

13. The process of claim 9 wherein $v_{vac.}$ is at least about 2.5 times the critical value, $v_{crit.}$, during the growth of the vacancy dominated regions.

14. The process of claim 13 wherein the ratio of $L_{vac.}/L_{int.}$ is at least about 0.08.

15. The process of claim 1 wherein the regions in which crystal lattice vacancies are the predominant intrinsic point defects have a radius, $R_{vac.}$, extending from the axis of the ingot towards the lateral surface which is at least about 50% of the radius, R, of the constant diameter portion of the crystal.

16. The process of claim 1 wherein the regions in which crystal lattice vacancies are the predominant intrinsic point defects have a radius, $R_{vac.}$, extending from the axis of the ingot towards the lateral surface which is at least about 90% of the radius, R, of the constant diameter portion of the crystal.

17. The process of claim 1 wherein the cooling rate of the ingot is controlled such that the regions are cooled from the temperature of solidification to a temperature, $T_A$, at which agglomerated intrinsic point defects nucleate, such that the regions are maintained at a temperature above $T_A$ for a time period of at least an effective dwell time, $t_{dw-eff.}$, required to prevent the formation of agglomerated intrinsic point defects in the interstitial dominated regions.

18. The process of claim 17 wherein the temperature, $T_A$, at which agglomerated interstitials nucleate is from about 850° C. to about 1,100° C.

19. The process of claim 17 wherein the temperature, $T_A$, at which agglomerated interstitials nucleate is from about 870° C. to about 970° C.

20. The process of claim 1 wherein region(s) in which silicon self-interstitial atoms are the predominant intrinsic point defects have an axial length, $L_{int.}$, which is at least about 25% of the radius, R, of the constant diameter portion of the crystal.

21. The process of claim 20 wherein the effective dwell time, $t_{dw-eff.}$, is at least about 20% of the dwell time required to allow a sufficient quantity of silicon self-interstitial atoms to diffuse to the surface of the ingot only to suppress the concentration of silicon self-interstitial atoms below a critical concentration required for agglomerated intrinsic point defects to nucleate, in an ingot wherein silicon self-interstitial atoms are the predominant intrinsic point defect throughout the entire constant diameter portion of an ingot.

22. The process of claim 1 wherein region(s) in which silicon self-interstitial atoms are the predominant intrinsic point defects have an axial length, $L_{int.}$, which is less than about twice the radius, R, of the constant diameter portion of the crystal.

23. The process of claim 22 wherein the effective dwell time, $t_{dw-eff.}$, is less than about 85% of the dwell time required to allow a sufficient quantity of silicon self-interstitial atoms to diffuse to the surface of the ingot only to suppress the concentration of silicon self-interstitial atoms below a critical concentration required for agglomerated intrinsic point defects to nucleate, in an ingot wherein silicon self-interstitial atoms are the predominant intrinsic point defect throughout the entire constant diameter portion of an ingot.

24. The process of claim 1 wherein region(s) in which silicon self-interstitial atoms are the predominant intrinsic point defects have an axial length, $L_{int.}$, which is about equal to radius, R, of the constant diameter portion of the crystal.

25. The process of claim 24 wherein the effective dwell time, $t_{dw\text{-}eff}$, is about 60% of the dwell time required to allow a sufficient quantity of silicon self-interstitial atoms to diffuse to the surface of the ingot only to suppress the concentration of silicon self-interstitial atoms below a critical concentration required for agglomerated intrinsic point defects to nucleate, in an ingot wherein silicon self-interstitial atoms are the predominant intrinsic point defect throughout the entire constant diameter portion of an ingot.

26. The process of claim 1 wherein the radius of the constant diameter portion of the ingot, R, is at least about 100 mm.

27. The process of claim 1 wherein the radius of the constant diameter portion of the ingot, R, is at least about 150 mm.

28. The process of claim 1 wherein the length of the constant diameter portion of the ingot, L, is at least about 400 mm.

29. The process of claim 1 wherein the length of the constant diameter portion of the ingot, L, is at least about 600 mm.

30. The process of claim 1 wherein the length of the constant diameter portion of the ingot, L, is at least about 1000 mm.

31. The process of claim 1 wherein the constant diameter portion of the ingot initially comprises at least about 2 vacancy dominated regions.

32. The process of claim 1 wherein the constant diameter portion of the ingot initially comprises at least about 4 vacancy dominated regions.

33. The process of claim 1 wherein the constant diameter portion of the ingot initially comprises at least about 6 vacancy dominated regions.

34. The process of claim 1 wherein the constant diameter portion of the ingot initially comprises at least about 8 vacancy dominated regions.

35. The process of claim 1 wherein the total quantity of vacancies in the initial vacancy dominated regions is greater than the total quantity of interstitials in the initial interstitial dominated regions.

36. The process of claim 1 further comprising quench cooling the ingot to a temperature less than a temperature at which agglomerated intrinsic point defects nucleate.

* * * * *